(12) United States Patent
Plumet et al.

(10) Patent No.: US 7,115,133 B2
(45) Date of Patent: Oct. 3, 2006

(54) SIMPLE-TO-USE SIZE MEASURER

(75) Inventors: Sylvie Plumet, Chaumont (FR); Saïd Moussa, Chamarandes-Choignes (FR)

(73) Assignee: Aesculap, (FR)

( * ) Notice: Subject to any disclaimer, the term of this patent is extended or adjusted under 35 U.S.C. 154(b) by 197 days.

(21) Appl. No.: 10/818,722

(22) Filed: Apr. 6, 2004

(65) Prior Publication Data

US 2004/0215205 A1    Oct. 28, 2004

(30) Foreign Application Priority Data

Apr. 24, 2003    (FR) .................................. 03 05061

(51) Int. Cl.
*A61B 17/58*    (2006.01)
(52) U.S. Cl. ........................ 606/102; 606/88
(58) Field of Classification Search ................ 606/102, 606/88
See application file for complete search history.

(56) References Cited

U.S. PATENT DOCUMENTS

| | | | | |
|---|---|---|---|---|
| 4,524,766 A | * | 6/1985 | Petersen ...................... | 606/88 |
| 4,567,886 A | * | 2/1986 | Petersen ...................... | 606/88 |
| 5,141,513 A | * | 8/1992 | Fortune et al. ............... | 606/96 |
| 5,364,401 A | * | 11/1994 | Ferrante et al. ............... | 606/84 |
| 5,417,694 A | | 5/1995 | Marik et al. .................. | 606/88 |
| 5,486,178 A | * | 1/1996 | Hodge .......................... | 606/82 |
| 5,562,675 A | * | 10/1996 | McNulty et al. ............... | 606/96 |
| 5,624,444 A | * | 4/1997 | Wixon et al. .................. | 606/88 |
| 6,013,081 A | | 1/2000 | Burkinshaw et al. .......... | 606/88 |
| 6,024,746 A | * | 2/2000 | Katz ............................ | 606/88 |
| 6,290,704 B1 | * | 9/2001 | Burkinshaw et al. .......... | 606/88 |
| 2004/0220583 A1 | * | 11/2004 | Pieczynski et al. ......... | 606/102 |

FOREIGN PATENT DOCUMENTS

JP    8-308857    11/1996

* cited by examiner

*Primary Examiner*—Bruce Snow
(74) *Attorney, Agent, or Firm*—Renner, Kenner, Greive, Bobak, Taylor & Weber

(57) ABSTRACT

A size measurer, comprising a main body with a sensor-head not fixed to the main body, so that a main pointer is moved in accordance with the adjustment opposite a range which includes several markers corresponding to the sizes of the available implants, characterised by the fact that it includes a slider fitted separately in relation to the main body, the slider including a first pointer and a second pointer, the first pointer being fitted in a such a way as to be moved, after the sliding of the slider, opposite the said range, and the second slider being moved, after the movement of the slider, opposite the gradations positioned on a fixed area in relation to the main body, the distance between the two points of the slider being such that when the first pointer is opposite the markers corresponding to one of the sizes of the available implants, the second pointer indicates by the gradations the height, in millimetres for example, of the posterior cut to be made in order that the implant is perfectly flush with the level of the anterior cortical.

4 Claims, 3 Drawing Sheets

SIMPLE-TO-USE SIZE MEASURER

TECHNICAL FIELD

This invention relates to a size measurer, that is to say a device which allows one to determine, amongst several sizes of available implants, (within a finite number however) the size of the optimum femoral implant to implant in a femur.

BACKGROUND ART

Currently, in order to determine the correct size, the surgeon has to have available a set of implants in different sizes and evaluate the optimum size of the femur before making the cut. In addition, it is difficult for him to know the impact of the choice of implant size on the cut of the bone and the position of the implant.

This invention aims to overcome these inconveniences by proposing a size measurer which allows the surgeon to determine very simply and very quickly, amongst a given, finite number of femoral implant sizes, first which size exactly corresponds to the femur on which the femoral implant should be implanted and subsequently, if, among those available, there is no size which corresponds exactly to that of the femur, which is the closest, and the exact place where the anterior cut along the femoral axis should be made in order to perfectly position the implant on the anterior cortical, sure of good positioning of the implant's trochlea and reducing patellar surges in vivo, whilst indicating the cut thickness more or less at the level of the posterior condyles.

DISCLOSURE OF THE INVENTION

According to the invention, the size measurer, incorporating a main body which has a sensor head independent of the main body so that a main pointer is moved according to the adjustment of a range opposite comprising several markers corresponding to the sizes of the implants available, is characterised by the fact that it comprises a casing fitted independently of the main body, the casing includes a first pointer and a second pointer, the first pointer being such that it can be moved, whilst the casing slides, opposite the said range, and the second casing moves, during the movement of the casing, opposite the gradings positioned on a fixed area in relation to the main body, the distance between the two pointers of the casing being such that when the first pointer is opposite one of the markers corresponding to one of the sizes of the available implants, the second pointer indicates the height on the graduations, for example in millimetres, of the cut to be made at the posterior so that the implant is perfectly flush to the level of the anterior cortical.

Thus, the surgeon, in order to determine the right implant amongst several sizes of implant, places the condyles on the tray, adjusts the sensor head as it reaches the anterior cortical, laid opposite the main pointer of the size to be chosen, and if the pointer isn't exactly opposite one of the available sizes, the casing must be slid along so that the first pointer is opposite one of the sizes, preferably the smallest size nearest to the main pointer, the second pointer then indicating, on the graduations formed on the main body, the height of the supplementary cut of the bone at the level of the posterior condyles, in order to adapt the chosen size perfectly. Thus the procedure is made very simple, without having to change the position of the measurer and simply by sliding the casing, by an adjustable knob for example.

It is preferable for the range to be on a plate, fixed to the sensor head in a roughly flat shape to be adapted to a femur of which the antero-posterior cut has already been made.

In this way, a particularly simple method of use can be obtained.

It is preferable that the main body includes a tray to receive the condyles, positioned opposite the sensor-head.

Thus it becomes very easy to take a measurement.

This invention also aims at a process of measuring the femur with a view to determining the size of the optimum implant amongst several available sizes.

According to the invention, the process is characterised by the fact that it comprises a stage which consists of, once the size in the upper part of the antero-posterior plan is determined, sliding a casing in order that a first pointer indicates the size selected and, at the same time, that a second pointer indicates the higher thickness of the plan of the cut at the level of the posterior condyles for a perfect adjustment at the level of the rear cortical of the implant of the chosen size.

BRIEF DESCRIPTION OF THE DRAWINGS

The figures in the drawings show one method of operating a measurer according to the invention, though not the only method.

PREFERRED EMBODIMENT FOR CARRYING OUT THE INVENTION

Figure 1:
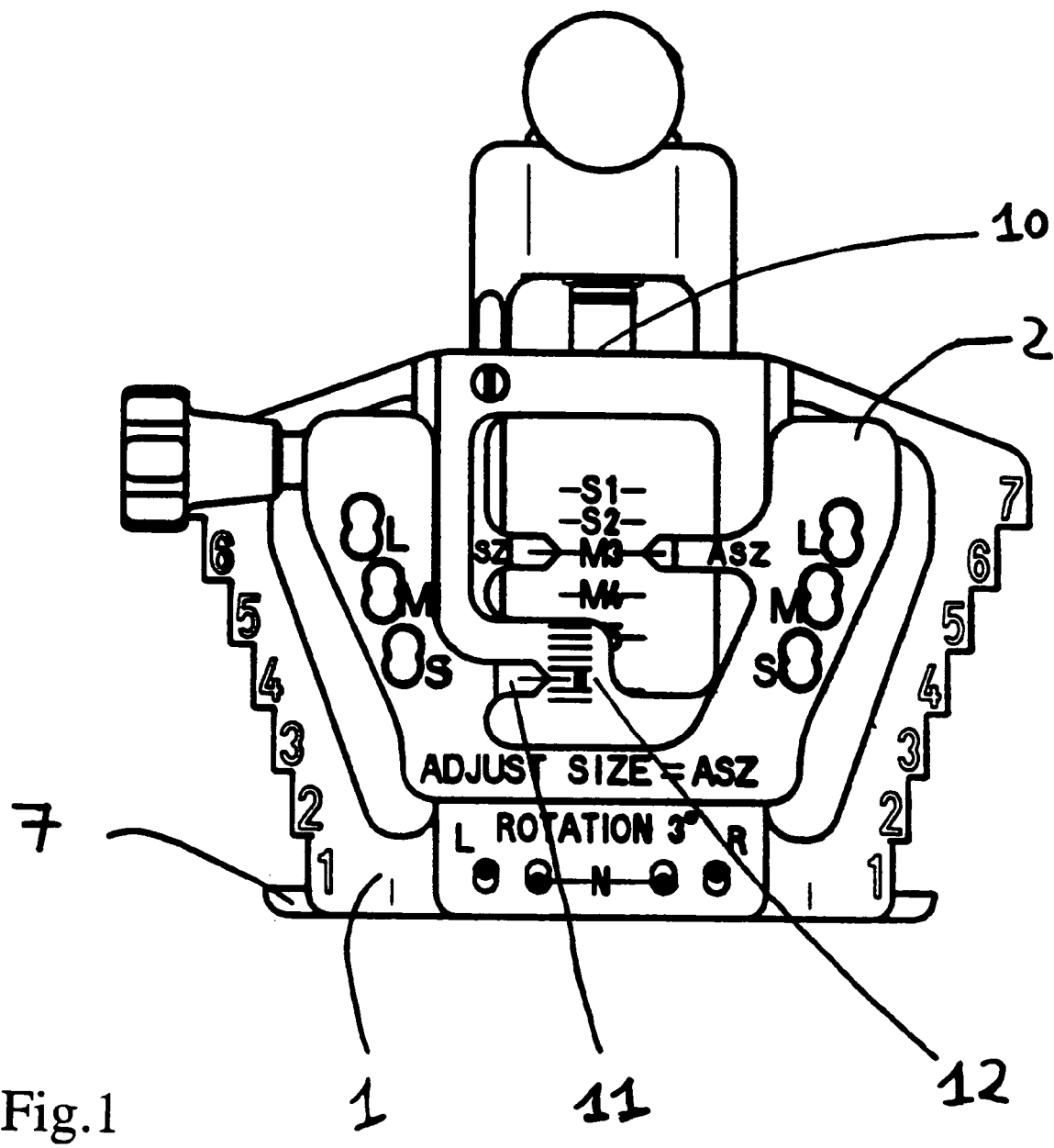
FIG. 1 is a view from the front of a measurer according to the invention.
Figure 2:
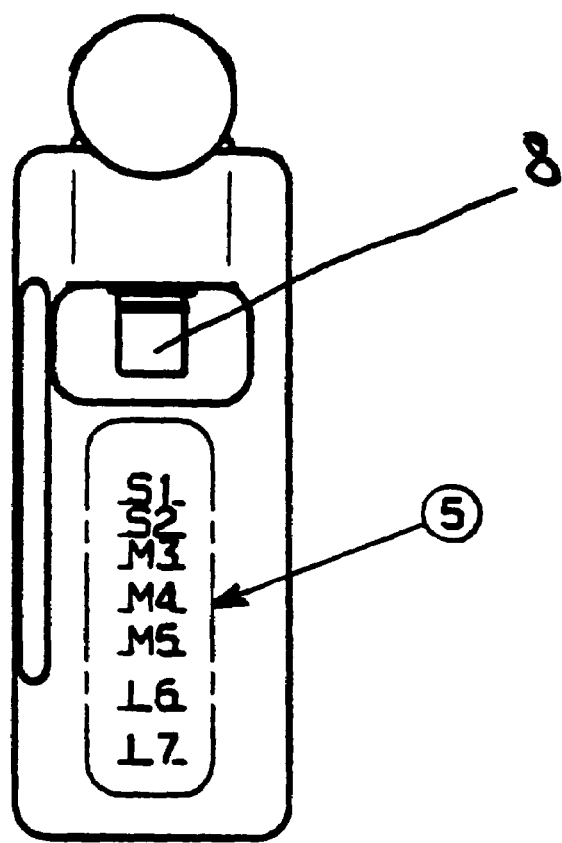
FIG. 2 is a partial view of the measurer shown in FIG. 1, showing the sensor-head and its graduated associated support.
Figure 4:
FIG. 4 is a perspective view showing the size measurer fitted to the distal end of a femur, of which the distal cut has already been made.

As can be seen from the figures, the measurer consists of a main body 1. This main body 1 includes a base plate 7 which is designed to connect with the condyles of the femur (see FIG. 4). A movable sensor-head 4 ensemble is fitted vertically as in FIG. 1 (the vertical direction here being the direction difined by the intersection of the medio-lateral and rear-posterior plans) and includes, in addition to the sensor-head 8, a plaque 5 marked with the reference points S1, S2, M3, M4, M5, L6 and L7 corresponding to the various sizes of femoral implant available.

Figure 3:
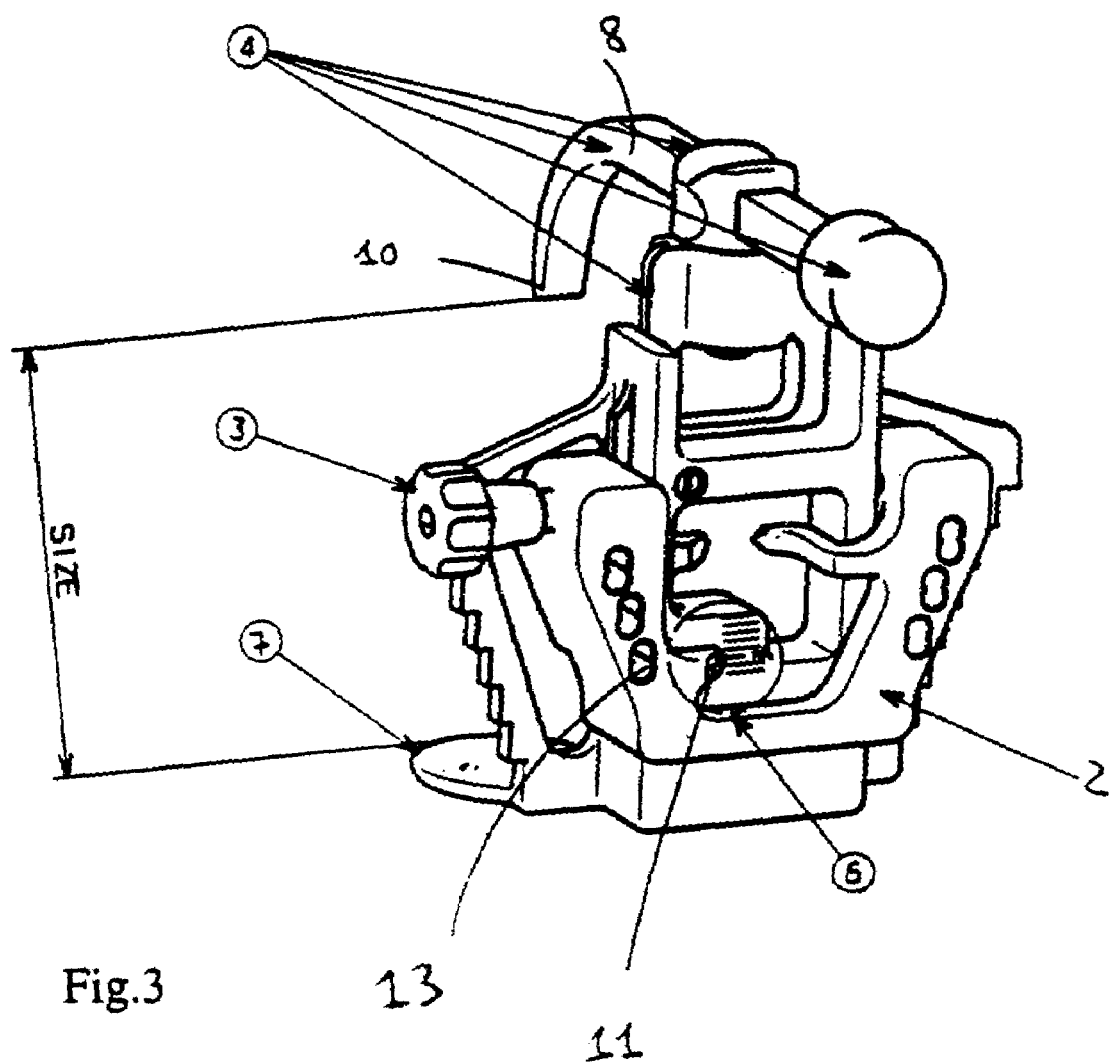
FIG. 3 is a perspective view of the measurer shown in FIG. 1.

The main body 1 also includes a main pointer SZ where the vertical distance (as in FIG. 3) to the plateau 7 is specified in advance, whilst also taking into account the total height of the plaque 5, to indicate the size of the implant corresponding to a posiiton of point 10 on the sensor-head 8.

Thus, once the point of the sensor-head is in contact with or just flush with the cortical of the femur, the pointer SZ indicates the exact size of the implant which will be neessary. It must be noted that in general the pointer will not be exactly facing one of the markers S, M or L but rather between two of these reference points.

In addition, a slider 2 is fitted on the main body, where the sliding movement in relation to the main body is free but can be fixed by an adjustable knob 3. This slider includes a first pointer ASZ and a second pointer 11. The dimensions of the slider and particularly the distances measured vertically as in FIG. 3, between the pointer ASZ and the holes 13 are chosen according to the dimensions of the sizes of the possible implants (S1, ..., L7) available on the measurer, to make it such that the second pointer, when the first pointer moves into the usable range (that is to say, facing the area of the plaque 5 incorporating the markers S1, . . . , L7), the second pointer moves opposite an area 6 fixed in relation to the main body, notably on the main body, this area including the gradations 12, in this case in millimetres, to indicate the discrepancy in relation to the chosen size, a discrepancy corresponding to the height of the cut to be made at the posterior level after one defines the size of the implant selected to be perfectly flush with the lower cortical.

The slider also includes a series of holes 13, grouped here in sizes S, M. L which facilitate the perfect positioning of the points which are inserted to pierce the bone with precise fixing points as a cutting guide to making the anterior, posterior, anterior chamfer and posterior chamfer cuts corresponding to the choice of the size of the implant selected by the preceding use of the measurer.

The invention claimed is:

1. A femoral implant size measurer, comprising:
    a main body, comprising a main pointer;
    a sensor head assembly comprising a sensor head and a range with markers corresponding to the sizes of available implants, said sensor head assembly being movable in relation to the main body so that said main pointer can be moved opposite said range with markers; and
    a slider which can slide in relation to said main body, and including a first pointer and a second pointer, the first pointer being fitted to be moved, by the sliding of the slider opposite said range, while the second pointer is moved opposite a gradations area fixed in relation to the main body, the distance between the first and second pointers of the slider being such that when the first pointer is opposite the markers, the second pointer indicates, by the gradations, the height of the posterior cut to be made in order that the implant be flush with the level of the anterior cortical.

2. A measurer according to claim 1, characterised by the fact that the range is positioned on the plate, interdependant of the sensor-head and roughly level to be adapted to a femur when the distal cut has already been made.

3. A measurer according to claim 2, characterised by the fact that the main body includes a plateau to receive the condyles, positioned opposite to the sensor-head.

4. A measurer according to claim 1, characterised by the fact that the main body includes a plateau to receive the condyles, positioned opposite to the sensor-head.

* * * * *